United States Patent [19]

Farb

[11] Patent Number: 5,888,996
[45] Date of Patent: Mar. 30, 1999

[54] INHIBITION OF NMDA RECEPTOR ACTIVITY AND MODULATION OF GLUTAMATE-MEDIATED SYNAPTIC ACTIVITY

[75] Inventor: David H. Farb, Cambridge, Mass.

[73] Assignee: Trustees of Boston University, Boston, Mass.

[21] Appl. No.: 559,442

[22] Filed: Nov. 15, 1995

Related U.S. Application Data

[63] Continuation-in-part of Ser. No. 507,757, Jul. 26, 1995, abandoned.

[51] Int. Cl.$^6$ .................................................. A61K 31/56
[52] U.S. Cl. ........................... 514/182; 514/177; 514/178; 514/179
[58] Field of Search .................................. 514/182, 177, 514/178, 179

[56] References Cited

U.S. PATENT DOCUMENTS

| 5,212,167 | 5/1993 | Farb | 514/178 |
| 5,366,968 | 11/1994 | Farb | 514/178 |

FOREIGN PATENT DOCUMENTS

| WO 93/04687 | 4/1991 | WIPO . |
| WO 93/05786 | 4/1993 | WIPO . |
| WO 94/27608 | 12/1994 | WIPO . |

OTHER PUBLICATIONS

CA 122:23982 Irwinet et al, 1994.
CA 121:125584 Park–Chung et al, 1994.
CA 119:86563 Bowlby, 1993.
CA 119:20512 Farb, Mar. 18, 1993.
CA 117:185114 Malone, 1992.
Wong, M., and Moss, R.L., "Patch–Clamp Analysis of Direct Steroidal Modulation of Glutamate Receptor–Channels", *Jour. of Neuroendocrinology*, 6:347–355, (1994).
Bowlby, M.R., "Pregnenolone Sulfate Potentiation of N–Methyl–D–aspartate Receptor Channels in Hippocampal Neurons", *Mol. Pharmacol.*, 43(5):813–819, (1993).
Irwin, R. P., et al., "Steroid Potentiation and Inhibition of N–Methyl–D–Aspartate Receptor–Mediated Intracellular Ca++ Responses: Structure–Activity Studies," *J. Pharm. and Experimental Therapeutics*, 271(2) :677–682 (1994).
Gyermek, L., et al., "Structure–Activity Relationship of Some Steroidal Hypnotic Agents," *Steroids. CCX.,* 11:117–125 (1968).
Wu, F.–S., et al., "Pregnenolone Sulfate: A Positive Allosteric Modulator at the N–Methyl–D–aspartate Receptor," *Molecular Pharmacology*, 40:333–336 (1991).
Park–Chung, M., et al., "3α–Hydroxy–5β–pregnan–20–one Sulfate: A Negative Modulator of the NMDA–Induced Current in Cultured Neurons," *Molecular Pharmacology*, 46:146–150 (1994).
Wieland, S., et al., "Anxiolytic Activity of the Progesterone Metabolite 5α–pregnan–3α–ol–20–one," *Brain Research*, 565:263–268 (1991).
Belelli, D., et al., "Anticonvulsant Profile of the Progesterone Metabolite 5α–pregnan–3α–ol–20–one," *European Journal of Pharmacology*, 166:325–329 (1989).
Lan, N. C., et al., "Neuroactive Steroid Actions at the $GABA_A$ Receptor," *Hormones and Behavior*, 28:537–544 (1994).

*Primary Examiner*—Rebecca Cook
*Attorney, Agent, or Firm*—Hamilton, Brook, Smith & Reynolds, P.C.

[57] ABSTRACT

The present invention relates to a method of inhibiting N-methyl-D-aspartate (NMDA) glutamate receptor-mediated ion channel activity (NMDA receptor activity), comprising contacting a neuronal cell (e.g., hippocampal neuron, spinal cord cell) with an effective amount (e.g., 1 to 500 μM) of a derivative of pregnenolone sulfate. Derivatives of pregnenolone sulfate that inhibit NMDA receptor activity include pregnenolone sulfate in which the A ring includes at least one double bond or is fully unsaturated, the double bond at the C5–C6 position is reduced, the moiety at the C3, C10, C11 or C13 position is modified, alone or in combination. It further relates to pregnenolone sulfate derivatives which have modifications at other positions (e.g., C5, C7, C10, C16, C17, C18, C19, C20, C21), alone or in combination, and are inhibitors of NMDA recepteor activity. The pregnenolone sulfate derivatives differ from pregnenolone sulfate at least one position. The present invention also relates to a method of modulating or altering (e.g., potentiating; inhibiting) excitatory glutamate-mediated synaptic activity comprising contacting neurons with pregnenolone sulfate and derivatives of pregnenolone sulfate.

17 Claims, 5 Drawing Sheets

INHIBITION OF NMDA RECEPTOR ACTIVITY AND MODULATION OF GLUTAMATE-MEDIATED SYNAPTIC ACTIVITY

RELATED APPLICATIONS

This application is a Continuation-in-Part application of U.S. application Ser. No. 08/507,757, filed Jul. 26, 1995, abandoned, entitled "Inhibition of NMDA Receptor Activity" by David H. Farb, which claims priority to U.S. Provisional Application, 60/001,439, filed on Jul. 24, 1995, entitled "3α-Hydroxy-5β-Pregnan-20-One Sulfate: A Negative Modulator of the NMDA-Induced Current in Cultured Neurons" by David H. Farb and claims the benefit thereof.

FUNDING

Work described herein was funded by grants from the National Institutes of Mental Health (Grant MH-49469). The United States government has certain rights in the invention.

BACKGROUND

L-Glutamate is thought to be the major excitatory neurotransmitter in the vertebrate central nervous system and is known to activate at least three major, pharmacologically distinct classes of glutamate-gated ion channels: N-methyl-D-aspartate (NMDA), α-amino-3-hydroxy-5-methyl-4-isoxazole-propionate (AMPA), and kainate receptors. These three inotropic receptors are named according to their selective agonists.

NMDA receptors have attracted particular attention because of their importance in normal brain function and in pathophysiological conditions such as epilepsy and cerebral ischemia (Rothman, S. M. and Olney, J. W., *Trends Neurosci.*, 10:299–302 (1987)). The NMDA receptor appears to be essential for the induction of long-term potentiation (Collingridge, G. L. and Bliss, T. V. P., *Trends Neurosci.*, 10:288–293 (1987)), a proposed underlying mechanism for learning and memory (Madison, D. V., et al., *Annu. Rev. Neurosci.*, 14:379–397 (1991)), ischemic cell death, epilepsy, and other neurological disorders (Simon, R. P., et al., *Science* 226:850–852 (1984); Choi, D. W., *J. Neurosci.* 10:2493–2501 (1990) such as hypoxic neuronal damage (Simon, R., et al., *Science*, 226:850–852 (1984)), schizophrenia (Carlsson, M., et al., *Trends Neurosci.*, 13:272–276 (1990); Watchel, H., et al., *Trends Pharmacol. Sci.*, 11:219–220 (1990)) and excitotoxicity (Onley, J., et al., *Brain Res.*, 221:207–210 (1981)). The integral channel of the NMDA receptor is permeable to Na+, K+, and $Ca^{2+}$. NMDA receptor activation thus increases intracellular $Ca^{2+}$ in neuronal cells, and this process is thought to evoke glutamate-induced neurotoxicity (Madison, D. V., et al., *Annu. Rev. Neurosci.*, 14:379–397 (1991)).

Thus, inhibition of NMDA receptor activity would be useful for protecting against various disorders including glutamate-induced neurotoxicity.

SUMMARY OF THE INVENTION

The present invention relates to a method of inhibiting N-methyl-D-aspartate (NMDA) glutamate receptor-mediated ion channel activity (NMDA receptor activity), comprising contacting a neuronal cell (e.g., hippocampal neuron, spinal cord cell) with an effective amount (e.g., 1 to 500 μM) of a derivative of pregnenolone sulfate. Derivatives of pregnenolone sulfate that inhibit NMDA receptor activity include pregnenolone sulfate derivatives in which the A ring includes at least one double bond or is fully unsaturated, pregnenolone sulfate derivatives in which the double bond at the C5–C6 position is reduced, pregnenolone sulfate in which the moiety at the C3, C10, C11 or C13 position is modified, alone or in combinations thereof. It further relates to pregnenolone sulfate derivatives which have modifications at other positions (e.g., C5, C7, C10, C16, C17, C18, C19, C20, C21), alone or in combination, and are inhibitors of NMDA receptor activity. The pregnenolone sulfate derivatives differ from pregnenolone sulfate at least one position.

In one embodiment the present invention relates to a method for inhibiting NMDA glutamate receptor mediated ion-channel activity comprising contacting a neuronal cell with an effective amount of a derivative of pregnenolone sulfate wherein the derivative is selected from the group consisting of: 3α-hydroxy-5β-pregnan-20-one sulfate (5β3αS), 3β-hydroxy-5β-pregnan-20-one sulfate (5β3βS), 3α-hydroxy-5α-pregnan-20-one sulfate (5α3αS), 3α-hydroxy-5α-pregnan-20-one hemisuccinate (5β3α hemisuccinate), 17β-estradiol hemisuccinate, 11β-OH-pregnenolone sulfate and androsterone sulfate.

The present invention also relates to a method of inhibiting toxic effects associated with activation of the NMDA receptor in neurons (e.g., hippocampal neurons, spinal cord cells), comprising contacting the neurons with a derivative of pregnenolone sulfate selected from the group consisting of: 5β3αs, 5β3βs, 5α3αs, 5β3α hemisuccinate, 17β-estradiol hemisuccinate, 11β-OH-pregnenolone sulfate and androsterone sulfate.

Thus, the ability to selectively inhibit the NMDA receptor across nerve cell membranes offers the means for pharmacological intervention in various glutamate-induced conditions such as excitotoxicity, epilepsy, cerebral ischemia and stroke.

The present invention also relates to a method of modulating or altering (e.g., potentiating; inhibiting) excitatory glutamate-mediated synaptic activity comprising contacting neuronal cells with pregnenolone sulfate or a derivative of pregnenolone sulfate. In one embodiment, the invention relates to a method of potentiating excitatory glutamate-mediated synaptic activity comprising contacting neuronal cells with pregnenolone sulfate or a derivative of pregnenolone sulfate (e.g., dehydroepiandrosterone sulfate). In another embodiment, the invention relates to a method of inhibiting excitatory glutamate-mediated synaptic activity comprising contacting neuronal cells with a derivative of pregnenolone sulfate (e.g. 5β3αS).

The ability to modulate the excitatory glutamate-mediated synaptic activity offers the means for pharmacological intervention in various glutamate-mediated synaptic activities such as neuropathic pain, drug withdrawal/dependency, epilepsy, chronic neurodegenerative diseases (Parkinson's Disease, Alzheimer's Disease, AIDS, Huntington's Disease) amyotrophic lateral sclerosis and anxiety disorders. The compounds described herein can also be used as anticonvulsants, sedative or hypnotic agents or as muscle relaxants.

In addition, the present invention relates to a method of identifying an agent or compound which modulates glutamate-mediated synaptic activity. For example, neurons are contacted with a steroid described herein which modulates (potentiates or inhibits) excitatory glutamate-mediated synaptic activity and the affinity of the steroid to its receptor (NMDA) is established. The compound to be assessed is added and assessed for its ability to compete with the binding site of the steroid.

DETAILED DESCRIPTION OF THE INVENTION

The present invention is based on the discovery that derivatives of pregnenolone sulfate, a potentiator of NMDA receptor activity, inhibit NMDA receptor activity. Derivatives of pregnenolone sulfate that inhibit NMDA receptor activity include pregnenolone sulfate in which the A ring contains at least one double bond or is fully unsaturated, the double bond at the C5–C6 position is reduced, a moiety at the C3, C10, C11 or C13 positions is modified alone or in combinations thereof. Additional pregnenolone sulfate derivatives include those which are modified at other positions, such as C5, C7, C10, C16, C17, C18, C19, C20 and C21, alone or in combination. Examples of pregnenolone sulfate derivatives include: 5β3αs, 5β3βs, 5α3αs, 5β3α hemisuccinate, 17β-estradiol hemisuccinate, 11β-OH-pregnenolone sulfate and androsterone sulfate.

In the methods of the present invention, a derivative of pregnenolone sulfate is contacted with a neuronal cell. A neuronal cell includes those from the central nervous system (e.g., spinal cord cell, hippocampal cell).

In the methods of the present invention, a sufficient amount of a pregnenolone sulfate derivative is administered to inhibit NMDA receptor activity (i.e., an effective amount). Preferably the concentration of the pregnenolone sulfate derivative is about 1–500 μM. A more preferred range is from about 50 to about 250 μM.

Inhibition of NMDA receptor activity includes partial or total inhibition of the effects of NMDA receptor activity (e.g., excitotoxicity).

In addition to the derivatives of pregnenolone sulfate described herein, one skilled in the art can predict with a high degree of certainty that other modifications of these pregnenolone sulfate derivatives are also useful for inhibiting the NMDA receptor-mediated ion channel activity. These modifications can be in addition to or independent of (in lieu of) those at the A ring, the C5–C6 double bond, the C3, C10, C11 or C13 position. Those skilled in the art recognize that pregnenolone sulfate derivatives with modifications at other positions such as the C5, C7, C10, C16, C17, C18, C19, C20 and/or C21 position are inhibitors of NMDA receptor activity. In addition, some modifications can increase the inhibitory effects on the NMDA receptor and, as a result, reduced concentrations of these derivatives are needed. For example, the polar OH group of 11β-OH-pregnenolone sulfate can be substituted with aliphatic or aromatic alcohol.

Such derivatives include, for example, derivatives in which the sulfate at position 3 of the steroid skeleton is replaced by an alkyl sulfate. The alkyl sulfates include, for example, methyl, ethyl and propyl sulfates.

Alternatively, steroid sulfate derivatives in which the sulfate at position 3 of the steroid skeleton is replaced with a phosphate, methylthiophosphonothioate, or sulfamate. In the instance of the sulfamate, linkage to the parent steroid would be through an amino group substituted for the hydroxyl at carbon 3.

Alternatively, steroid sulfate derivatives in which the sulfate at position 3 of the steroid skeleton is replaced with a sulfonate can be used. These include, for example, methyl, ethyl, propyl, isopropyl and dimethyl sulfonates.

Additionally, derivatives in which the sulfate at position 3 of the parent steroid skeleton is replaced by an alkyl or aryl sulfate that is joined to the steroid skeleton via an ether, thioether, nitrogen atom, or carbon—carbon bond, and in which the sulfate is separated from the steroid by an alkyl or aryl group can be used. Alternatively, derivatives in which the alkyl sulfate at position 3 of the steroid skeleton is replaced with an alkyl or aryl phosphate, methylthiophosphonothioate, sulfonate, or sulfamate can be used. For example, one or more sulfate or sulfonate groups could be added to the benzoate moiety of 17β-estradiol benzoate or pregnanolone benzoate.

A third useful class of derivatives have a dicarboxylic acid in place of the sulfate at position 3 linked to the parent steroid skeleton by an ester bond. The dicarboxylic acids include alkyl and aryl dicarboxylates. The alkyl include, for example, methyl, ethyl, propyl, butyl, pentyl, hexyl, heptyl and octyl, and the aryl dicarboxylates include ortho, para and meta benzoates. For example, one or more carboxylate groups could be added to the benzoate moiety of 17β-estradiol benzoate or pregnanolone benzoate.

A fourth useful class of derivatives have one or more negative charges introduced by, for example, a carboxylate, sulfate, phosphate, sulfonate or methylthiophosphonothioate derivative of a sugar in place of the sulfate at position 3 of the parent steroid (i.e., pregnenolone sulfate). These include, for example, pregnanolone-3-D(or L)-glucosiduronate or pregnanolone-3-D(or L)-phosphoglucosiduronate. Specific examples of the modifications discussed above include 3α-hydroxy-16-imino-5β-17-aza-androstan-11-one or 3α-hydroxy-5α-pregnane-11,20-dione hemisuccinate.

Figure 1:
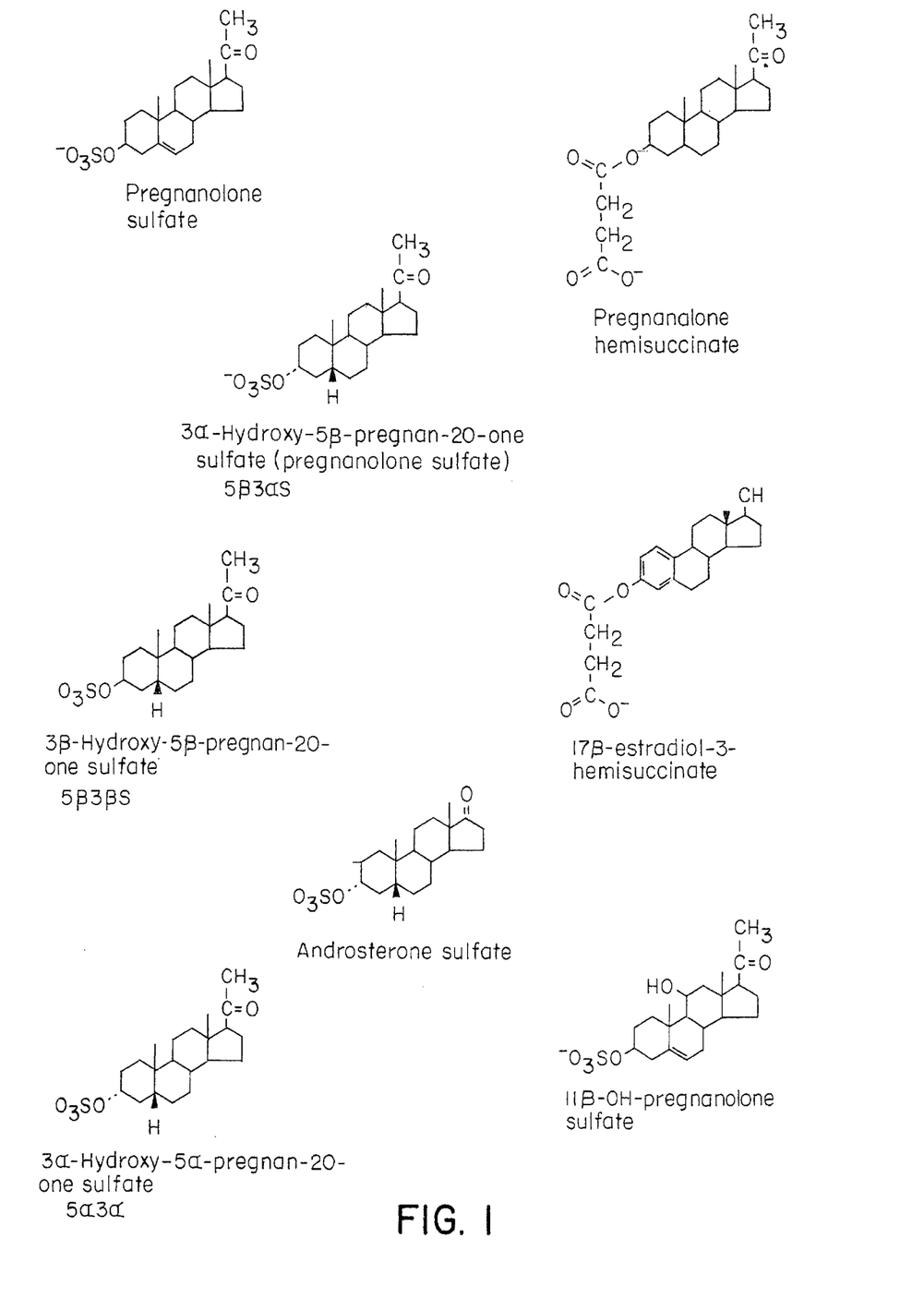
FIG. 1 is a diagram showing the general structures of pregnenolone sulfate, 3α-hydroxy-5β-pregnan-20-one sulfate (5β3αS), 3β-hydroxy-5β-pregnan-20-one sulfate (5β3βS), 3α-hydroxy-5α-pregnan-20-one sulfate (5α3αS), 5β3α hemisuccinate, 17β-estradiol hemisuccinate, 11β-OH-pregnenolone sulfate and androsterone sulfate.

The neurosteroid pregnenolone sulfate acts as a positive allosteric modulator at the NMDA receptor and inhibits the kainate, the AMPA, the glycine, and the γ-aminobutyric acid (GABA) responses of chick spinal cord neurons (Wu, F. S., et al., *Mol. Pharmacol.* 40:333–336 (1991)). It was surprising that particular derivatives of pregnenolone sulfate, such as 5β3αS (FIG. 1) inhibit the NMDA receptor-induced current.

The NMDA receptor is subject to modulation through several pharmacologically distinct sites (Monaghum, D. T., et al., *Annu. Rev. Pharmacol.*, 29:365–402 (1989); Wong, E. H. F. and Kemp, J. A., *Annu. Rev. Pharmacol. Toxicol.*, 81:401–525 (1991)), including those for glycine, $Mg^{2+}$, and polyamines (Ransom, R. W. and Stec, N. L., *J. Neurochem.*, 51–830–836 (1988)). Moreover, the dissociative anesthetics dizocilpine (MK-801), phencyclidine (PCP), and ketamine all produce a voltage-dependent and use-dependent blockade of ion channel activity (Hucttner, J. E. and Bean, B. P., *Proc. Natl. Acad. Sci. USA*, 85:1307–1311 (1988); Lerma, J., et al., *Neurosci. Lett.*, 123:187–191 (1991)).

As described in Example 1, 5β3αS inhibits the NMDA-induced response by a voltage- and agonist-independent, noncompetitive mechanism that is different from that of open channel blockers such as MK-801. In addition, androsterone sulfate, inhibited the NMDA-induced response (see Table 1). 5β3αS, a sulfated form of naturally occurring 5β3α, inhibits both the NMDA and the non-NMDA receptor-mediated responses as measured by whole cell voltage clamp recordings. 100 μm 5β3αS rapidly and reversibly inhibits the response to 30 μm NMDA by 66%, 50 μM kainate by 37%, and 25 μM AMPA by 29%. Application of 60 μM nonsulfated 5β3α does not produce any significant effect on the NMDA response, demonstrating that the sulfate moiety is important for the effect of 5β3αS on the NMDA response. The effect of 5β3αS on the NMDA response is concentration dependent; the $EC_{50}$ is 62 μM. 5β3αS reduces the maximum NMDA response with little effect on the NMDA $EC_{50}$ indicating that antagonism of the NMDA response by 5β3αS is noncompetitive. The fact that 5β3αS inhibition of the NMDA response is neither agonist nor voltage dependent demonstrates that 5β3αS does not act as an open channel blocker.

Based on the ability of 5β3αS to exhibit a robust inhibitory effect on the NMDA response, the mechanism of action of 5β3αS on the NMDA response was further studied. As described in Example 1, inhibition of the NMDA response by 5β3αS is not reduced by the addition of a maximal concentration (10 μM) of glycine, indicating that 5β3αS does not act via the glycine recognition site. The inhibitory action of 5β3αS on the NMDA and non-NMDA receptors provides a basis for inhibiting glutamate receptor-induced seizures and excitotoxic cell death.

Example 3 describes additional pregnenolone sulfate derivatives which were examined by electrophysiology for inhibition of NMDA receptor activity. In addition, as described in Example 4, pregnenolone sulfate derivatives which inhibit NMDA receptor activity also protect against the excitotoxicity effects associated with NMDA receptor activity.

Associated with stroke, hypoxia neuronal damage and ischemia is cell death thought to result from effects associated with activation of the NMDA receptor by L-glutamate. Therefore, it is possible to prevent cell death by interfering with L-glutamate-induced NMDA-receptor activation. The present invention relates to a method of reducing neuronal cell death resulting from L-glutamate activation of the NMDA receptor, comprising contacting neuronal cells with a derivative of pregnenolone sulfate selected from the group consisting of: pregnenolone sulfate in which the A ring includes at least one double bond, pregnenolone sulfate in which the C5–C6 double bond is reduced, pregnenolone sulfate in which the moiety at C3, C10, C11, or C13 is modified and combinations thereof wherein the derivative is present in a concentration sufficient to inhibit the effects of activation of the NMDA receptor on neuronal cells.

The studies described herein not only reveal another mechanism of non-competitive blockade of the NMDA-induced current, but give a basis for understanding the structural requirements of steroids for NMDA receptor activation. The results described herein demonstrate that particular derivatives or analogues of pregnenolone sulfate represent a novel class of broad spectrum antagonists of excitatory amino acid receptors. These sulfated steroids can be used as anticonvulsant or anti-excitotoxic therapeutic agents.

As further described herein, the effects of steroids on glutamate-mediated synaptic responses have been studied. As described in Example 5, pregnenolone sulfate (PS), which potentiates the NMDA response to exogenously applied NMDA (see U.S. Pat. No. 5,212,167), potentiates spontaneous excitatory post-synaptic currents (EPSCs) in cultures of rat hippocampal neurons. The 5β3αS compound, which inhibits the NMDA response to exogenously applied NMDA, inhibits spontaneous EPSCs in cultures of rat hippocampal neurons. Using whole-cell recording methods, cells were voltage-clamped at −70 mV. Drug solutions were applied to single neurons by pressure ejection from 7-barrel pipets. EPSC potentiation by PS is concentration-dependent, with an $EC_{50}$ of 5.6 μM and maximum potentiation of 198.2%. An analog of PS, 11-keto PS, has no effect on EPSCs, suggesting the effect of PS on EPSCs is specific. When EPSCs mediated by NMDA receptors are blocked with the specific NMDA receptor antagonist APV (40 μM), the potentiation of EPSCs by 100 μM PS is reduced. Conversely, when EPSCs mediated by non-NMDA glutamate receptors are blocked with the specific non-NMDA receptor antagonist DNQX (10 μM), 100 μM PS produces a greater potentiation of EPSCs (453%). These results indicate that PS primarily potentiates EPSCs mediated by NMDA receptors. The effects of PS on EPSCs agree with those of PS on the response induced by exogenously applied NMDA. These observations provide further evidence that neurosteroids such as PS can exert direct neuromodulatory effects on excitatory synaptic transmission in the CNS.

The present invention also relates to a method of modulating or altering (e.g., potentiating; inhibiting) excitatory glutamate-mediated synaptic activity comprising contacting neuronal cells with pregnenolone sulfate or a derivative of pregnenolone sulfate. In one embodiment, the invention relates to a method of potentiating excitatory, glutamate-mediated synaptic activity comprising contacting neuronal cells with pregnenolone sulfate or a derivative of pregnenolone sulfate (e.g., dehydroepiandrosterone sulfate). In another embodiment, the invention relates to a method of inhibiting excitatory glutamate-mediated synaptic activity comprising contacting neuronal cells with a derivative of pregnenolone sulfate (e.g. 5β3αS).

The ability to modulate the excitatory glutamate-mediated synaptic activity offers the means for pharmacological intervention in various glutamate-mediated synaptic activities such as neuropathic pain, drug withdrawal/dependency, epilepsy, chronic neurodegenerative diseases (Parkinson's Disease, Alzheimer's Disease, AIDS, Huntington's Disease) amyotrophic lateral sclerosis and anxiety disorders. The compounds described herein can also be used as anticonvulsants, sedative or hypnotic agents or as muscle relaxants.

In addition, the present invention relates to a method of identifying an agent or compound which modulates glutamate-mediated synaptic activity. For example, neurons are contacted with a steroid described herein which modulates (potentiates or inhibits) excitatory glutamate-mediated synaptic activity and the affinity of the steroid to its receptor (NMDA) is established. The compound to be assessed is added and assessed for its ability to compete with the binding site of the steroid.

The invention is further illustrated in the following examples, which are not intended to be limiting in any way.

EXAMPLE 1

3α-hydroxy-5β-pregnan-20-one sulfate (5β3αS) and Aldosterone Sulfate Inhibit the NMDA-Induced Response Materials and Methods Cell cultures. Cultures of dissociated spinal cord neurons were prepared as previously described (Farb, D. H., et al., *J. Cell Biol.*, 80:651–661 (1979)). Briefly, the dissociated cells from 7-day chick embryos were plated on collagen-coated 35-mm tissue culture dishes in Eagle's minimum essential medium supplemented with 2.4 mM glutamine, 10% (v/v) heat-inactivated horse serum, 5% (v/v) chick embryo extract and antibiotics. Cultures were maintained in a humidified atmosphere of 5% $CO_2$, 95% air at 37°. Cytarabine (1 $\mu$M) was added to the culture medium after 36 hr. of the initial plating to inhibit the proliferation of non-neuronal cells. One day later, this medium was replaced with a similar medium supplemented with 20.5 mM glucose, 19 mM KCl, and 2.5% chick embryo extract. Fresh medium was added twice weekly. Cultured neurons were used in experiments within 2–4 weeks after plating.

Electrophysiology. Experiments were carried out in 35-mm tissue culture dishes on the stage of an inverted phase contrast microscope. Whole cell currents were recorded by the whole cell variant of the patch clamp technique (Hamill, O. P., et al., *Pfagers Arch.* 891:85–100 (1981)). Patch electrodes had tip openings of about 2 $\mu$M and resistances of 3–8 MΩ using an intracellular solution comprised of the following (in mM): 140 CsCl, 11 EGTA, and 10 HEPES (pH adjusted to 7.2 with CsOH). In experiments in which a high concentration of glycine was used, the intracellular solution was replaced with a low chloride (10 mM) pipette solution. This solution contained the following (in mM): 140 potassium gluconate, 10 KCl, 8 sodium gluconate, 11 EGTA, and 10 HEPES (pH adjusted to 7.2 with KOH). To prevent a marked run-down of NMDA-induced current at high NMDA concentrations, 4 mM potassium ATP was included in the intracellular solution. The bath solution contained the following (in mM): 150 NaCl, 4 KCl, 1 $CaCl_2$, and 10 HEPES (pH adjusted to 7.2 with NaOH). No glycine was added to the solutions containing NMDA, because no additional glycine was required to obtain a robust NMDA response, and there was no effect of a maximal concentration (10 $\mu$M) of glycine on 5β3αS inhibition of the NMDA response. All experiments were performed at room temperature (23°–25° C.).

Recordings were made using an Axopatch 1B patch clamp apparatus (Axon Instruments, Burlingame, Calif.). Cells with series resistances greater than 10 MΩ were rejected. After partial compensation, series resistances were between 3.5 and 6 MΩ. The holding potential was maintained at −70 mV unless otherwise noted. Currents were filtered at 1 kHz using an eight-pole Bessel filter (−3 dB) and digitized (40 ms/point) using an on-line data acquisition system (pClamp, Axon Instruments).

Drug solutions were applied to single neurons by pressure ejection (15 psi) from seven-barrel pipettes. Seven-barrel pressure pipettes were positioned approximately 50 $\mu$M from the neuronal soma. Under these conditions, the drug solution in the pressure pipette rapidly and effectively replaces the solution surrounding the target neurons with less than 10% dilution (Choi, D. W., et al., *Nature* (Lond.) 269:342–344 (1977); Chan, C. Y., et al., *Life Sci.*, 83:2061–2069 (1983); Chan, C. Y. and Farb, D. H., *J. Neurosci.*, 5:2365–2373 (1985)). All drugs were obtained from Sigma, with the except of AMPA hydrobromide (Research Biochemicals) and steroids (Steraloids). Stock solutions of steroids were prepared in dimethyl sulfoxide, the final concentration of which was 0.5% (v/v). To obviate the possible effects of dimethyl sulfoxide on the relevant agonist-induced currents, all other drug solutions including NMDA, kainate, AMPA and external buffer (in the pressure pipette) also contained 0.5% dimethyl sulfoxide.

The degree of modulation of the amino acid response by steroid, the percentage change, is expressed as $[(I'/I)-1] \times 100\%$, where I is the average of control responses obtained from the same cell before application and after washout of steroid and I' is the agonist-induced current in the presence of steroid. Throughout, results are expressed as mean±S.E.; statistical comparison of groups was carried out using Student's t test.

Results

Figure 2:
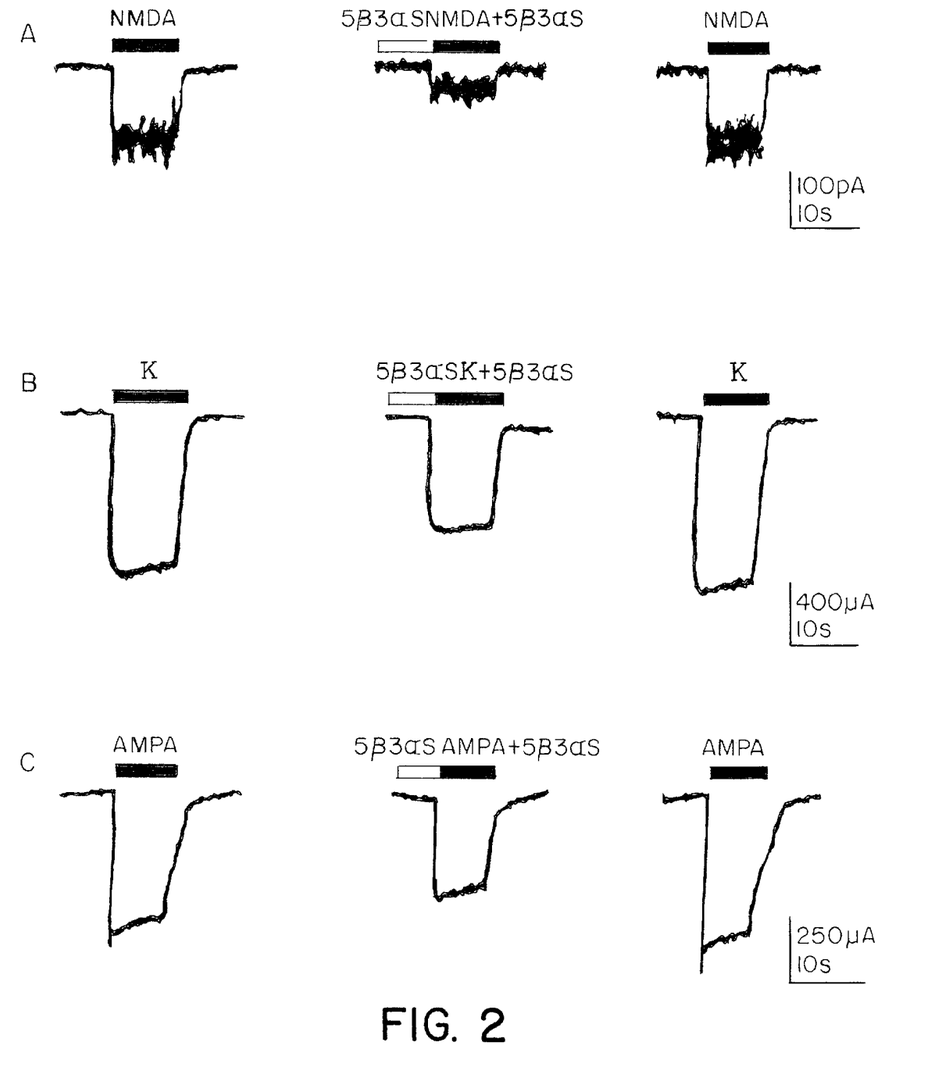
FIG. 2 displays traces of the effects of 100 μM 5β3αS on currents induced by NMDA, kainate and AMPA at holding potentials of −70 mV; the horizontal bar above each trace indicates the period of drug application.

Currents elicited by NMDA, kainate, and AMPA were recorded in primary cultures of chick spinal cord neurons by the whole cell variant of the patch clamp technique. Previously, it has been shown that pregnenolone sulfate potentiates the NMDA-induced whole cell current while inhibiting kainate and AMPA-induced currents (Wu, F. S., et al., *Mol. Pharmacol.* 40:333–336 (1991)). Suprisingly, 5β3αS produced an opposite modulatory effect, inhibiting the NMDA response. The effects of 100 $\mu$M 5β3αS on currents induced by NMDA, kainate, and AMPA at holding potentials of −70 mV are illustrated in FIG. 2. The response to 30 $\mu$M NMDA was inhibited (66.1±2.7%, n=5) when 5β3αS was applied simultaneously with NMDA. The onset and recovery of inhibition was rapid, and the inhibitory effect of 5β3αS was fully reversible after a wash period of 3–4 min. 100 $\mu$M 5β3αS also rapidly and reversibly inhibited 25 $\mu$M AMPA-(29.0±3.1%, n=4) and 50 $\mu$M kainate- (37.4+/−4.7%, n=4) induced currents. Application of 5β3αS alone did not produce any direct response.

Results are shown in Table 1 (values are means+/−S.E.; number of cells is indicated in parentheses). As shown in Table 1, aldosterone sulfate, also inhibited the NMDA-induced response. However, not all sulfated steroids inhibit the NMDA response. Dehydroepiandrosterone sulfate (DHEAS) only slightly potentiated the NMDA response (28.8±8.8% potentiation, n=4). Application of 50 $\mu$M non-sulfated 5β3α (which represents its maximal solubility in the external buffer) did not produce any significant effect on the 30 $\mu$M NMDA-induced current (3.6±8.4% potentiation, n=4), indicating that the sulfate moiety is important for the effect of 5β3αS on the NMDA response.

Figure 3:
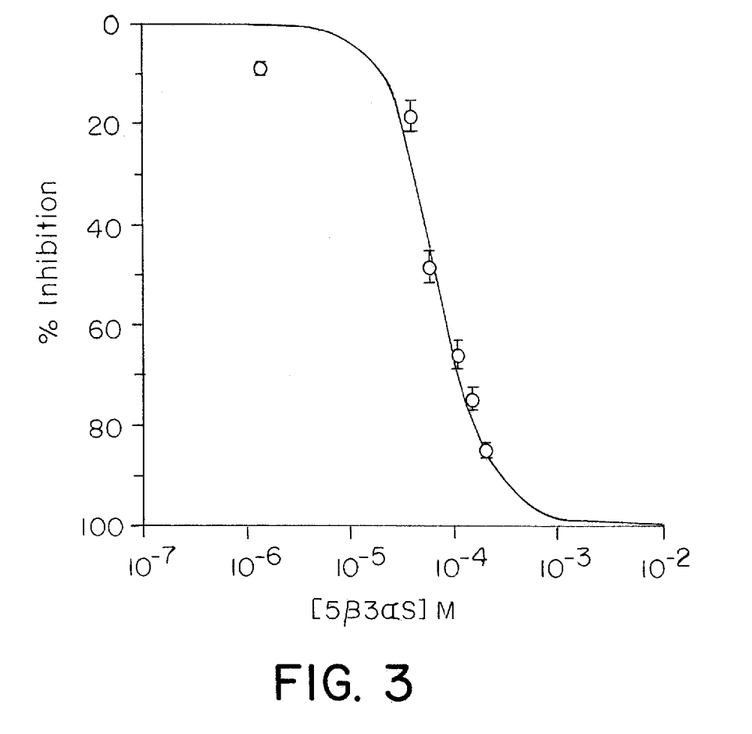
FIG. 3 is a graph of molar concentration of 5β3αS versus % inhibition indicating the concentration-response curve for inhibition of NMDA response by 5β3αS (mean of four to eight experiments).

To quantitatively evaluate the potency and efficacy of 5β3αS for NMDA receptors, pooled data were used to construct the concentration-response curve for inhibition of the 30 $\mu$M NMDA response by 5β3αS. As shown in FIG. 3, 5β3αS produced a concentration-dependent blockade of the current induced by 30 $\mu$M NMDA, and curve-fit analysis revealed an $EC_{50}$ of 62.1 $\mu$M and maximal inhibition of 101.1%.

To investigate the mechanism of inhibition by 5β3αS, pooled data were used to construct a concentration-response curve for NMDA in the presence and absence of 50 $\mu$M 5β3αS. To obviate cell-to-cell variability with respect to the maximal current induced by NMDA, all responses were normalized to the peak current induced by 100 $\mu$M NMDA. 5β3αS markedly reduced the NMDA maximal response with little effect on the NMDA $EC_{50}$. (In the absence of 5β3αS, $EC_{50}$=155.6 μM, $I_{max}$=2.56, and $n_H$=1.01). In the presence of 5β3αS, $EC_{50}$=105,7 μM, $I_{max}$=1.10, and $n_H$=1.46) NMDA $EC_{50}$ values are close to the $EC_{50}$ reported for cultured chick motor neurons (O'Brien, R. J. and Fishbach, G. D., *J. Neurosci.*, 6:3257–3283 (1986)). This result suggests that the action of 5β3αS on the NMDA response is noncompetitive in nature and that 5β3αS acts through a site distinct from the NMDA recognition site.

Because the noncompetitive NMDA antagonists such as MK-801 act on the ion channel in a use-and voltage-dependent manner (Hucttner, J. E. and Bean, B. P., *Proc. Natl. Acad. Sci. USA*, 85:1307–1311 (1988)), the voltage dependence of the effect of 5β3αS on the NMDA-induced current was tested. The average inhibition produced by 100 μM 5β3αS at +50 mV (62.0±2.8%, n=5) was not significantly different from that at −70 mV (63.2±2.7%, n=5) (p>0.05, paired t test). This result indicates that the blockade by 5β3αS of the NMDA response is voltage independent. Use dependence was not observed on the time scale of these experiments; the first application of 5β3αS in the presence of NMDA elicited an immediate blockade of both peak and plateau responses, and the recovery of the NMDA response after washout of 5β3αS was rapid.

The response of the NMDA receptor is positively modulated by glycine, and glycine may be an absolute requirement for receptor function (Johnson, J. W. and Ascher, P., *Nature (Lond.)* 325:529–531 (1987)). Some inhibitors of the NMDA response, such as 7-chlorokynurenic acid, act by blocking the glycine site of the NMDA receptor (Wong, E. H. F. and Kemp, J. A., *Annu. Rev. Pharmacol. Toxicol.*, 81:401–525 (1991)). To determine whether 5β3αS acts as a competitive antagonist at the glycine recognition site, the effect of 5β3αS on the NMDA responses in the presence of a saturating concentration (10 μM) of glycine was examined. 50 μM 5β3αS still reduced the current induced by 30 μM NMDA with added glycine. Moreover, the average inhibition by 5β3αS (51.3±3.5%, n=4) was not significantly different from that in the absence of glycine (49.1±3.4%, n=4) (p>0.5, unpaired t test). This result is consistent with the view that the effect of 5β3αS on the NMDA-induced current is not mediated by the glycine recognition site.

Discussion

The highly lipophilic nature of the steroids and the evidence that phospholipids are capable of binding steroids with high specificity (Majewska, M. D., *Biochem. Pharmacol.* 35:3781–3788 (1987)) raise the possibility that the effect of 5β3αS is mediated by interactions with the membrane lipids surrounding the NMDA receptor protein. However, we have shown that another pregnenolone sulfate analogue, DHEAS, has only a slight effect (28.8% potentiation) on the NMDA response in comparison with the effect of pregnenolone sulfate, which potentiates the NMDA response by 197% (Wu, F. S., et al., *Mol. Pharmacol.* 40:333–336 (1991)). This finding argues that antagonism of the NMDA-induced current by 5β3αS is a specific effect.

There are a number of potential sites at which 5β3αS could exert its blocking action, including: 1) competitive inhibition at the NMDA binding site, 2) blockade of the NMDA receptor associated channel, or 3) noncompetitive inhibition or allosteric modulation at a distinct site.

First, competition of 5β3αS for the NMDA binding site cannot account for the observed result. The results show that the antagonism by 5β3αS of the NMDA-induced current is not attenuated by increasing concentrations of NMDA.

Second, blockage of a cation channel by a negatively charged molecule such as 5β3αS seems unlikely on theoretical grounds. The cloned NMDA receptor has a putative second transmembrane domain which is thought to be involved in lining the ion channel and is flanked by negatively charged amino acid residues (Moriyoshi, K., et al., *Nature* 354:31–37 (1991)). This would deter entry of a sulfated molecule into the channel. The lack of voltage and use dependent also suggests that the interaction of this compound with the inner channel wall is unlikely.

The NMDA receptor is thought to have a glycine recognition site (Johnson, J. W. and Ascher, P., *Nature (Lond.)* 325:529–531 (1987)) in addition to the agonist binding site. The inhibitory action of 5β3αS on the NMDA-induced currents cannot be surmounted by a saturating concentration of glycine. This experiment suggests that the steroid and glycine do not act at a common site.

Previously it has been shown that pregnenolone sulfate acts as a positive allosteric modulator at the NMDA receptor. Surprisingly, slight modifications of pregnenolone sulfate structure (reducing the C-5 position double bond, 3β-hydroxy to 3α-hydroxy) change the modulation of the NMDA receptor mediated response from a positive to a negative direction. Interestingly, 5β3αS produces opposite effects to pregnenolone sulfate only at the NMDA response. It elicits inhibitory effects similar to those of pregnenolone sulfate at the AMPA and kainate response. This result provides evidence that the structural requirements for modulation of NMDA and non-NMDA receptors by steroids are different. The ineffectiveness of non-sulfated 5β3α on the NMDA response demonstrates that sulfation converts an inactive steroid to an active steroid inhibitor, suggesting that steroid sulfotransferase could be an important enzyme in regulating NMDA receptor activity in the CNS.

The studies described herein not only reveal another mechanism of non-competitive blockade of the NMDA-induced current, but give a basis for understanding the structural requirements of steroids for NMDA receptor activation. The results described herein demonstrate that particular derivatives or analogues of pregnenolone sulfate represent a novel class of broad spectrum antagonists of excitatory amino acid receptors. The sulfated steroids can be used as anticonvulsant or anti-excitotoxic therapeutic agents.

TABLE 1

Effects of Steroids On the 30 μM NMDA-Induced Response

| Steroid | Change of response (%) |
|---|---|
| 5β3αS (100 μM) | −66.1 ± 2.7 (5) |
| 5β3α (10 μM) | −3.4 ± 3.5 (4) |
| (50 μM) | +3.6 ± 3.4 (4) |
| Androsterone sulfate (100 μM) | −18.1 ± 2.6 (3) |
| DHEAS (100 μM) | +28.8 ± 8.6 (4) |
| β-Estradiol benzoate (20 μM) | +24.3 ± 18 (3) |

EXAMPLE 2

3β-hydroxy-5β-pregnan-one sulfate (5β3βS) Inhibits NMDA Receptor Activity at a Specific Site of Action Experiments were conducted as described in Example 1 to determine the ability 5β3βS to inhibit NMDA, kainate and AMPA responses.

Application of 100 μM 5β3βS rapidly and reversibly inhibited responses to 30 μM NMDA by 59%, 50 μM kainate by 33% and 25 μM AMPA by 43%. 5β3βS alone at high concentrations (greater than or equal to 100 μM) often induced a small outward current. This current was not observed in the CsCl-containing intracellular solution, indicating that it is a $K^+$ current. Moreover, in the CsCl-containing solution, 5β3βS (100μM) still inhibited the NMDA response. In 2 cells, the average inhibition produced by 5β3βS was 49+/−5.0%, which was not significantly different from that measured in the KCl-containing intracellular solution (p>0.05, unpaired t test). This makes it unlikely that the 5β3βS-induced outward current could account for the inhibition of the NMDA response.

A stereoisomer of 5β3βS, 5α-pregnan-3β-ol-20-one sulfate (5α3βS) failed to inhibit (1+/−2.6%, n=6) the NMDA-induced current, suggesting that the interaction of 5β3βS with the NMDA receptor is stereospecific about carbon-5, but not at carbon-3. This stereoselectivity of action makes it unlikely that 5β3βS inhibits the NMDA receptor through a nonspecific mechanism, such as perturbation of the lipid bilayer proposed for short-chain alcohols (Lovinger et al., *Science*, 243:1721–1724 (1989), but supports instead the existence of a specific site of action.

To determine whether block of the NMDA response by 5β3βS is voltage-dependent, the effect of 100 μM 5β3βS on the current induced by 30 μM NMDA at two different holding potentials was examined. In 2 cells, the average inhibition produced by the 5β3βS is similar at −70 mV and +50 mV, indicating that the effect of 5β3βS on the NMDA response is not voltage-dependent. In addition, both block of the NMDA response and recovery from blockade by 5β3βS are rapid, suggesting that 5β3βS inhibition of the NMDA response is not agonist-dependent. Thus, the voltage-independent action of 5β3βS virtually excludes an interaction with the phencyclidine or $Mg^{2+}$ binding sites of the NMDA receptor.

To determine whether inhibition by 5β3βS of the NMDA response is mediated via the glycine recognition site, the effect of 5β3βS (100 μM) on the current induced by 30 μM NMDA in the presence of a saturating concentration (10 μM) of glycine was investigated. Inhibition of the NMDA response by 5β3βS did not significantly differ from that measured without added glycine (p>0.05, unpaired t test), indicating that the 5β3βS site is distinct from the glycine recognition site.

To investigate whether 5β3βS and pregnenolone sulfate (a potentiator of the NMDA response) act through the same site to modulate the NMDA response, the effect of 5β3βS on the current induced by 30 μM NMDA in the presence of a near-maximal concentration (200 μM) of pregnenolone sulfate. 200 μM 5β3βS still inhibited the peak NMDA response. In 4 cells, the average inhibition produced by 5β3βS was 50+/−4.4%, which was not significantly different from that (59+/−3.0%, n=4) measured in the absence of glycine (p>0.05, unpaired t test). Similarly, potentiation of the NMDA response by pregnenolone sulfate was still evident in the presence of a high concentration (200 μM) of 5β3βS. These results suggest that 5β3βS inhibits the NMDA response via a site distinct from the pregnenolone sulfate modulatory site.

EXAMPLE 3

Figure 4:
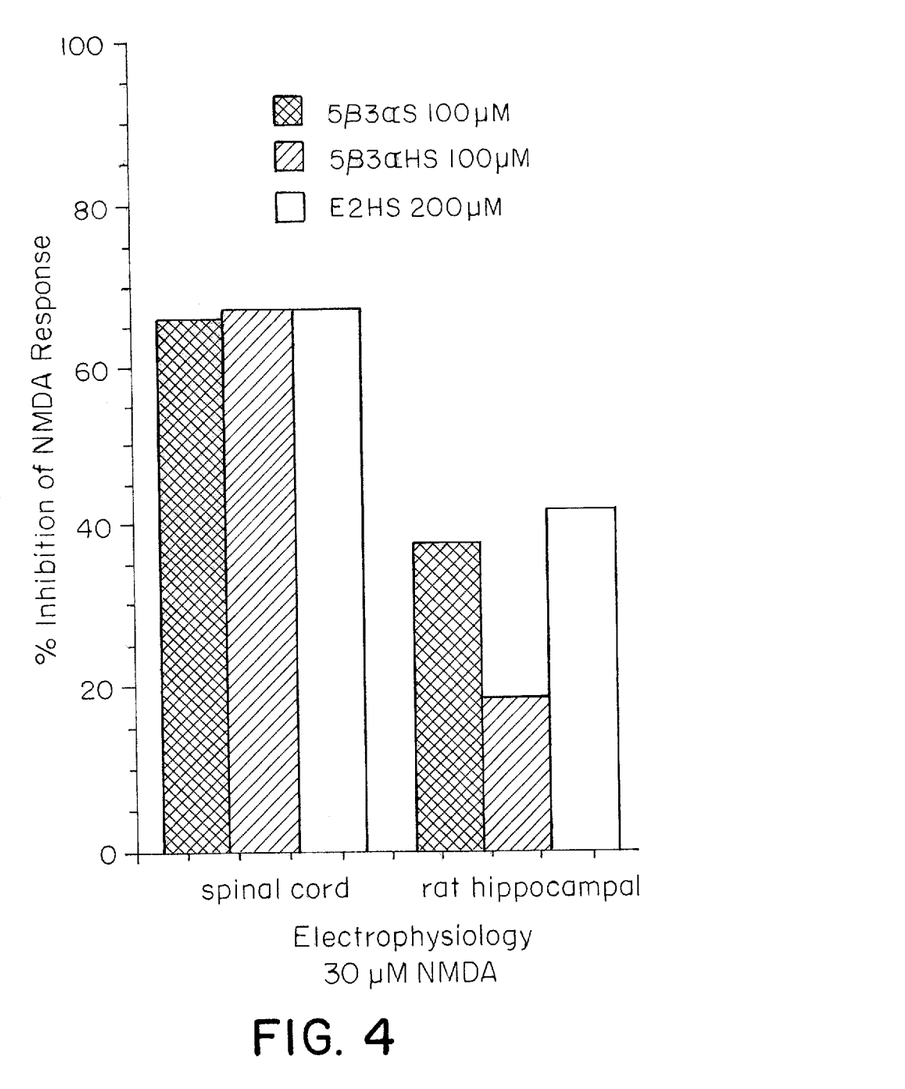
FIG. 4 is a bar graph of t inhibition of the NMDA response as measured by electrophysiology, demonstrating that 5β3αS, 5β3α hemisuccinate and 17β-estradiol hemisuccinate inhibit the NMDA response.

Additional Derivatives of Pregnenolone Sulfate which Inhibit NMDA Receptor Activity The electrophysiology of additional pregnenolone derivatives were analyzed as described in Example 1. The results of the following compounds: 5β3αS, 5β3α hemisuccinate, 17β-estradiol hemisuccinate, 11β-OH-pregnanolone sulfate, 5β3βS and 5α3αS are summarized in Table 2. FIG. 4 is a bar graph of electrophysiology versus % inhibition of the NMDA response demonstrating that 5β3αS, 5β3α hemisuccinate and 17β-estradiol inhibit the NMDA response.

As shown in FIG. 4, the % inhibition of NMDA response in rat hippocampal cells by 5β3α hemisuccinate was approximately 20%. In 2 of the 6 experiments conducted using 5f3α hemisuccinate, the compound was ineffective. However, in 4 of the 6 experiments the % inhibition of NMDA response in rat hippocampal cells was much larger. The results from all 6 experiments were averaged into the final result, which produced the lower % inhibition overall.

TABLE 2

Effects of Steroids On the NMDA Response

| | | % Change of response (30 μM NMDA-Induced Current or NMDA Response) | |
|---|---|---|---|
| Steroid | μM (Steroid) | chick spinal cord neurons | rat hippocampal neurons |
| 5β3αS | 100 | −66 ± 2.7 (5 cells) | −36.5 ± 2.1 (5 cells) |
| 5β3α hemisuccinate | 100 | −67 ± 2.0 (2 cells) | −18.0 ± 8.0 (6 cells) |
| 17β-estradiol hemisuccinate | 200 | −67 ± 9.5 (3 cells) | −41 ± 7.0 (4 cells) |
| 11β-OH-pregnenolone sulfate | 100 | −31 ± 2 (3 cells) | |
| 5β3βS | 100 | −59 ± 3 (4 cells) | |
| androsterone sulfate | 100 | −18 ± 2.6 (3 cells) | |

EXAMPLE 4

Inhibitors of NMDA Receptor Activity also Protect Against Excitotoxicity

Trypan blue exclusion was used to evaluate the ability of derivatives of pregnenolone sulfate to inhibit NMDA-induced cell death in primary neuronal cultures of rat hippocampal formation.

Mixed neuronal and glial cultures of hippocampal tissue were derived from fetal rats on day 18 of embryonic development and were maintained in culture for 16 to 24 days (Brewer, G. J., *Brain Res.*, 494: 65–74 (1989)). Care for the animals used in this study was in accordance with institutional guidelines. Hippocampal tissue from Sprague-Dawley rat pups was collected immediately following removal from dams sacrificed with $CO_2$ on embryonic day 18. Cells were dissociated by trituration in $Ca^{2+}$/$Mg^{2+}$ free Hank's basic salt solution supplemented with 4.2 mM bicarbonate, 1 mM sodium pyruvate, 20 mM HEPES, 3 mg/ml BSA, and pelleted by centrifugation (900 rpm, 3 min). The resulting pellet was suspended in DMEM supplemented with 2.4 mg/ml BSA, 26.5 mM sodium bicarbonate, 1 mM sodium pyruvate, 20 mM HEPES, 10% FBS, 100 units/ml penicillin, 100 μg/ml streptomycin, and a modification of Brewers B16 defined components (with 250 mM vitamin B12 and without catalase, glutathione, and superoxide dismutase) (Pike, C. J., et al., *Neurosci.* 13:1676–87 (1993)) and plated onto poly-L-lysine coated 24 well culture dishes (Nunclon) at a density of 15,000 cells/$cm^2$ and were maintained in a humidified incubator in 5% $CO_2$/95% air at 37° C. After 5 days in vitro, nonneuronal cell division was inhibited by exposure to $2\times10^{-6}$M cytosine arabinoside for 48 hrs. Cells were subsequently maintained in medium identical to that used for platting without BSA or FBS.

The number of living neurons was determined by assessing the ability of cells to exclude trypan blue 16 hrs. after the addition of drug solutions to the medium of individual culture wells (Dawson, V. L., et al., Proc. Natl. Acad. Sci. USA, 88:6368–6371 (1991)). Drugs were introduced to cultures in 100 µl of conditioned media, collected from experimental cultures just prior to treatment, to a final volume of 0.5 ml. NMDA was dissolved in DMEM at concentrations of 0–5 mM so that addition of 10 µl yielded final concentrations of 0–100 µM. MK-801, a positive control, was dissolved in DMEM at a concentration of 1 mM so that addition of 5 µl yielded a final concentration of 10 µM. Control cultures were exposed only to an equivalent volume of DMEM, and concentration of DMSO (0.5%). The concentrations of the pregnenolone sulfate derivatives were as follows: 10–100 µM 5β3αS, 100 µM 5β3α hemisucinate and 200 µM 17β-estradiol hemisuccinate.

After exposure to drugs, the medium was replaced by 0.1M sodium phosphate buffer/0.4% trypan blue. Cell death was assessed by counting the number of trypan blue positive and negative neurons in five high power fields per culture well with an inverted phase contrast microscope using both bright field and phase settings. Cell death is expressed as the ratio of the number of trypan blue positive to total number of cells counted in each well×100 (percent cell death).

Results

Figure 5:
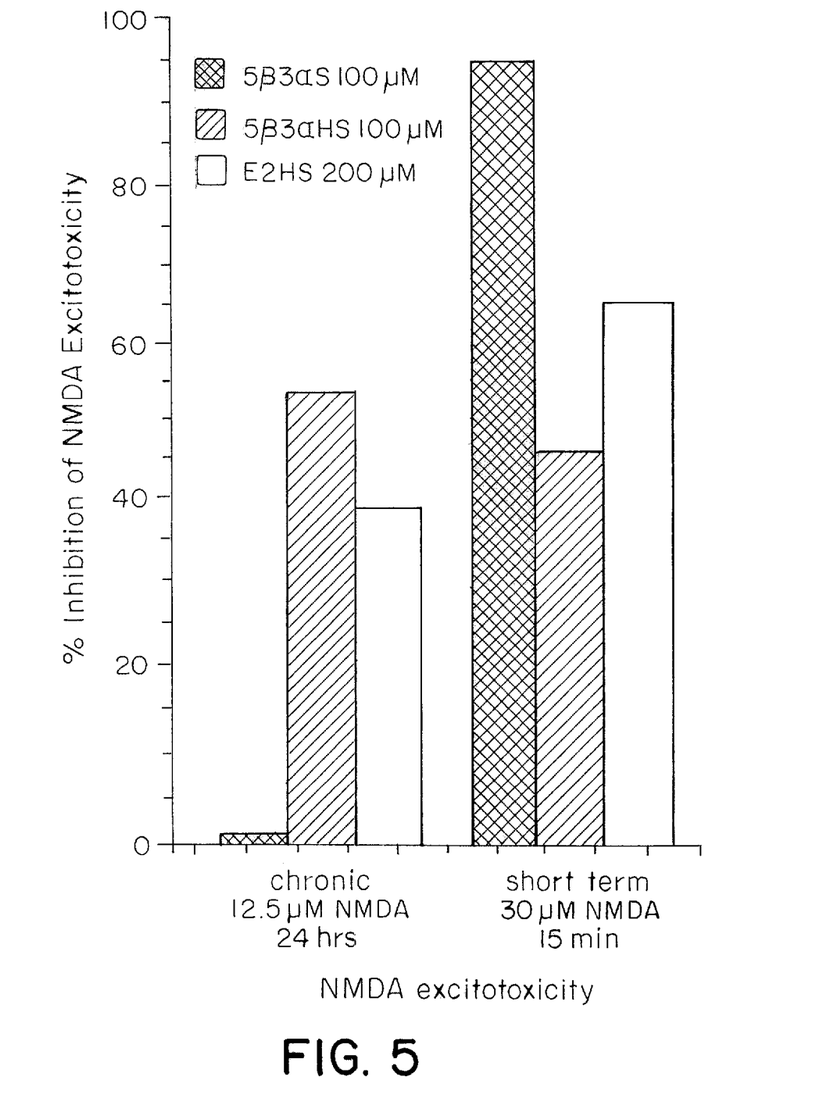
FIG. 5 is a bar graph of % inhibition of NMDA excitotoxicity (chronic and short term).

The results are illustrated in FIG. 5. 5β3αS protects against short term NMDA excitotoxicity but is ineffective against chronic NMDA-induced cell death. This may be due to instability of this compound. On occasion 5β3αS did show protection in the chronic exposure experiments but on average there was no effect.

5β3αS completely blocked the cell death due to NMDA when present during the exposure only, and was considerably less effective when present only after the exposure suggesting that protection is through a direct action on NMDA receptors. During and after as well as before, during, and after application of 5β3αS showed similar protection to the during only application. 5β3α hemisuccinate and 17β-estradiol hemisuccinate inhibit 50 and 40 percent of the cell death induced by chronic NMDA, and 46 and 65 percent of the cell death produced by short term exposure to NMDA. For both of these steroids more protection was seen in the excitotoxicity studies than might have been indicated by electrophysiology.

In addition, both of these steroids were most effective when present during NMDA exposure in the short term experiments. When present both during and after the NMDA insult the protection was somewhat less.

EXAMPLE 5

Modulation of Spontaneous Excitatory Postsynaptic Currents (EPSCs) by Preanenolone Sulfate and Its Derivatives in Cultured Neurons Primary cultures of hippocampal neurons were prepared from embryonic day 18 rats. Cultured neurons were used in experiments 2–3 weeks after plating.

Spontaneous excitatory postsynaptic currents were recorded by the whole-cell variant of the patch clamp technique. The pipet solution usually contained (in mM) KCl 10, EGTA 11, sodium gluconate 3, potassium gluconate 140 and HEPES 10, adjusted to pH 7.2 with KOH. The bath solution contained (in mM) NaCl 150, KCl 4, $CaCl_2$ 1, and HEPES 10, adjusted to pH 7.2 with NaOH. Because NMDA-induced currents are subject to voltage-dependent block by extracellular $Mg^{2+}$, no magnesium salts were added to the bath solution. All records were made with the cell membrane potential clamped at −70 mV, which is very close to the Cl- equilibrium potential. Therefore, IPSCs are not expected to be observed and spontaneous activity should consist of EPSCs. The complete blockage of spontaneous activity by the co-application of the NMDA receptor antagonist APV and the non-NMDA receptor antagonist DNQX argues that the observed spontaneous activity is glutamate receptor-mediated.

Drug solutions were applied to single neurons by pressure ejection (15 psi) from 7-barrel pipets (tip opening ~3–5 µm) positioned ~50 µm from the neuronal soma. In all experiments, neurons received a 40s application of either steroid or steroid plus antagonist(s), followed by 10–20s pulse of external buffer solution.

Results

As shown in Table 3, PS potentiates spontaneous EPSCs, and 5βαS inhibits spontaneous EPSCs, in cultures of rat hippocampal neurons. The analogue of PS, 11-keto PS has no effect on EPSCs. The percentage potentiation produced by 100 µM 11-keto PS is 19±15% (n=4). This suggests that the effect of PS on EPSCs is specific. The effect of some metabolites of PS were also examined on EPSCs.

Most of embryonic rat hippocampal neurons maintained in cell culture and assayed between 10–21 days after plating exhibit spontaneous excitatory postsynaptic currents (EPSCs) in the $Mg^{2+}$ free extracellular solution. The endogenous neurosteroid pregnenolone sulfate potentiates reversibly EPSCs in primary cultures of voltage-clamped rat hippocampal neurons. The effect of EPSCs is dose-dependent, with an $EC_{50}$ of 11.9 µM and maximal potentiation of 223%. When EPSCs mediated by NMDA receptors are blocked with the specific NMDA receptor antagonist APV, the potentiation of EPSCs by PS is reduced. Conversely, when EPSCs mediated by non-NMDA glutamate receptors are blocked with the specific non-NMDA receptor antagonist DNQX, PS produces a greater potentiation of ESCs. These results indicate that PS primarily potentiates EPSCs mediated by NMDA receptors. The effects of PS on EPSCs agree with those of PS on the response induced by exogenously applied NMDA. These observations provide further evidence that neurosteroids such as PS have direct neuromodulatory effects on excitatory synaptic transmission in the CNS. This is the first demonstration of modulation of excitatory synaptic currents by neurosteroids.

TABLE 3

Effects of steroids on EPSCs. Holding potential is −70 mV. Steroids are applied as described in Methods. Values are means ± SEM. Number of cells is indicated in parentheses.

| Steroid | Structure | Change of response (%) |
|---|---|---|
| PS (100 μM) |  | +198 ± 33 (5) |
| Dehydroepiandro-sterone sulfate (100 μM) |  | +136 ± 30 (3) |
| 11-keto PS (100 μM) |  | +19 ± 15 (4) |
| 5β-pregnan-3α-ol-20-one sulfate (100 μM) |  | −30 ± 4 (4) |
| 5α-pregnan-3α-ol-20-one (1 μM) |  | −18 ± 7 (4) |
| 5β-pregnan-3β-ol-20-one (1 μM) |  | +8 ± 8 (4) |

TABLE 3-continued

Effects of steroids on EPSCs. Holding potential is -70 mV. Steroids are applied as described in Methods. Values are means ± SEM. Number of cells is indicated in parentheses.

| Steroid | Structure | Change of response (%) |
|---|---|---|
| Progesterone (100 $\mu$M) | [structure with CH$_3$, C=O] | $-64 \pm 9$ (4) |

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method for inhibiting N-methyl-D-aspartate glutamate receptor mediated ion-channel activity, comprising administering to a patient in need thereof an effective amount of a compound represented by the following structural formula:

wherein:

ring A has zero to three double bonds;

$R^1$ is —OH, =O, or a negatively charged group;

$R^2$ is —CH$_3$, or is absent when ring A has three double bonds;

$R^3$ is —H, —OH, =O, or —OR';

R' is an aliphatic or aromatic group; and

$R^4$ is —OH, =O or —COCH$_3$.

2. The method of claim 1, wherein said compound is 5β3αS, 5β3βS, 5α3αS, androsterone sulfate, 17β-estradiol hemisuccinate, 5β3α hemisuccinate or progesterone.

3. The method of claim 1, wherein the effective amount is a concentration of from about 1 to about 500 $\mu$M.

4. The method of claim 3, wherein the effective amount is a concentration of from about 50 to about 250 $\mu$M.

5. A method of inhibiting the toxic effects associated with activation of the N-methyl-D-aspartate receptor in neurons, comprising administering to a patient in need thereof an effective amount of a compound represented by the following structural formula:

wherein:

ring A has zero to three double bonds;

$R^1$ is —OH, =O, or a negatively charged group;

$R^2$ is —CH$_3$, or is absent when ring A has three double bonds;

$R^3$ is —H, —OH, =O, or —OR';

R' is an aliphatic or aromatic group; and $R^4$ is —OH, =O or —COCH$_3$.

6. The method of claim 5, wherein said compound is 5β3αS, 5β3βS, 5α3αS, androsterone sulfate, 17β-estradiol hemisuccinate, 5β3α hemisuccinate or progesterone.

7. The method of claim 5, wherein the effective amount is a concentration of from about 1 to about 500 $\mu$M.

8. The method of claim 7, wherein the effective amount is a concentration of from about 50 to about 250 $\mu$M.

9. The method of claim 5, wherein the neurons are hippocampal cells or spinal cord cell.

10. A method of reducing neuronal cell death resulting from L-glutamate activation of the N-methyl-D-aspartate receptor, comprising administering to a patient in need thereof an effective amount of a compound represented by the following structural formula:

wherein:

ring A has zero to three double bonds;

$R^1$ is —OH, =O, or a negatively charged group;

$R^2$ is —CH$_3$, or is absent when ring A has three double bonds;

$R^3$ is —H, —OH, =O, or —OR';
R' is an aliphatic or aromatic group; and
$R^4$ is —OH, =O or —COCH$_3$.

11. The method of claim 10, wherein said compound is 5β3αS, 5β3βS, 5α3αS, androsterone sulfate, 17β-estradiol hemisuccinate, 5β3α hemisuccinate or progesterone.

12. The method of claim 10, wherein the effective amount is a concentration of from about 1 to about 500 μM.

13. A method for inhibiting seizures associated with activation of the N-methyl-D-aspartate receptor comprising administering to a patient in need thereof an effective amount of a compound represented by the following structural formula:

wherein:
ring A has zero to three double bonds;
$R^1$ is —OH, =O, or a negatively charged group;
$R^2$ is —CH$_3$, or is absent when ring A has three double bonds;
$R^3$ is —H, —OH, =O, or —OR';
R' is an aliphatic or aromatic group; and
$R^4$ is —OH, =O or —COCH$_3$.

14. The method of claim 13, wherein said compound is 5β3αS, 5β3βS, 5α3αS, androsterone sulfate, 17β-estradiol hemisuccinate, 5β3α hemisuccinate or progesterone.

15. A method for inhibiting excitotoxic cell death associated with activation of the N-methyl-D-aspartate receptor comprising administering to a patient in need thereof an structural formula:

wherein:
ring A has zero to three double bonds;
$R^1$ is —OH, =O, or a negatively charged group;
$R^2$ is —CH$_3$, or is absent when ring A has three double bonds;
$R^3$ is —H, —OH, =O, or —OR';
R' is an aliphatic or aromatic group; and
$R^4$ is —OH, =O or —COCH$_3$.

16. The method of claim 15, wherein said compound is 5β3αS, 5β3βS, 5α3αS, androsterone sulfate, 17β-estradiol hemisuccinate, 5β3α hemisuccinate or progesterone.

17. A method for inhibiting N-methyl-D-aspartate glutamate receptor mediated ion-channel activity, comprising administering to a patient in need thereof an effective amount of 11β-hydroxypregnenolone sulfate.

* * * * *

UNITED STATES PATENT AND TRADEMARK OFFICE
CERTIFICATE OF CORRECTION

PATENT NO. : 5,888,996
DATED : March 30, 1999
INVENTOR(S) : David H. Farb

It is certified that error appears in the above-identified patent and that said Letters Patent is hereby corrected as shown below:

In Claim 1, column 17, line 52, the phrase "R1 is an aliphatic or aromatic group" should read --R' is an aliphatic or aromatic group--.

In Claim 11, column 19, line 6, "5l3α" should read --5β3α--.

In Claim 15, column 20, line 3, after the word "an" the phrase --effective amount of a compound represented by the following-- should be inserted.

Signed and Sealed this

Twentieth Day of July, 1999

*Attest:*

Q. TODD DICKINSON

*Attesting Officer*   Acting Commissioner of Patents and Trademarks